United States Patent [19]

Holt

[11] 4,454,095
[45] Jun. 12, 1984

[54] AUTOMATIC CHEMICAL ANALYSIS DEVICES AND METHODS

[75] Inventor: John K. Holt, Ft. Pierce, Fla.

[73] Assignee: Harbor Branch Foundation, Inc., Fla.

[21] Appl. No.: 400,442

[22] Filed: Jul. 21, 1982

[51] Int. Cl.³ .................... G01N 21/00; G01N 35/04
[52] U.S. Cl. .......................................... 422/64; 422/65;
422/68; 422/63; 422/83; 73/864.82; 436/43
[58] Field of Search ................. 73/864.82; 198/560,
198/561, 803; 414/412; 422/63–65, 67, 68, 81,
83, 86, 88; 436/43, 47–49, 54, 145, 146

[56] References Cited

U.S. PATENT DOCUMENTS

| | | | |
|---|---|---|---|
| 1,194,990 | 8/1916 | Gaynor | 198/803 |
| 3,302,452 | 2/1967 | Leslie | 422/65 X |
| 3,322,958 | 5/1967 | Heiss | 422/64 X |
| 3,783,694 | 1/1974 | Otte et al. | 73/864.82 X |
| 4,226,119 | 10/1980 | Buser | 73/864.82 |

Primary Examiner—Michael S. Marcus
Assistant Examiner—Michael S. Gzybowski
Attorney, Agent, or Firm—Carroll F. Palmer

[57] ABSTRACT

An automatic chemical analysis device particularly designed for determination of carbon content in liquid samples comprises a turret with peripheral cavities to receive and transport tubular encased liquid sample ampoules, a base plate on which the turret is journaled for rotation, a conveyor to deliver the encased ampoules into the turret cavities, an index unit to position ampoules at a work station, a sealable chamber into which encased ampoules may be inserted, a plunger to raise the encased ampoules into the chamber, a purge tube extending into the chamber from above, a gas supply to the purge tube and a piston to move the purge tube up and down in the chamber.

The method of analysis comprises breaking the tops of ampoules when positioned in the chamber by lowering the purge tube and then flowing a gas through the tube into the liquid sample in the opened ampoule and then out the chamber to a gas analyzer. Successive samples are moved by the turret to the work station for automated, repeated analysis.

8 Claims, 6 Drawing Figures

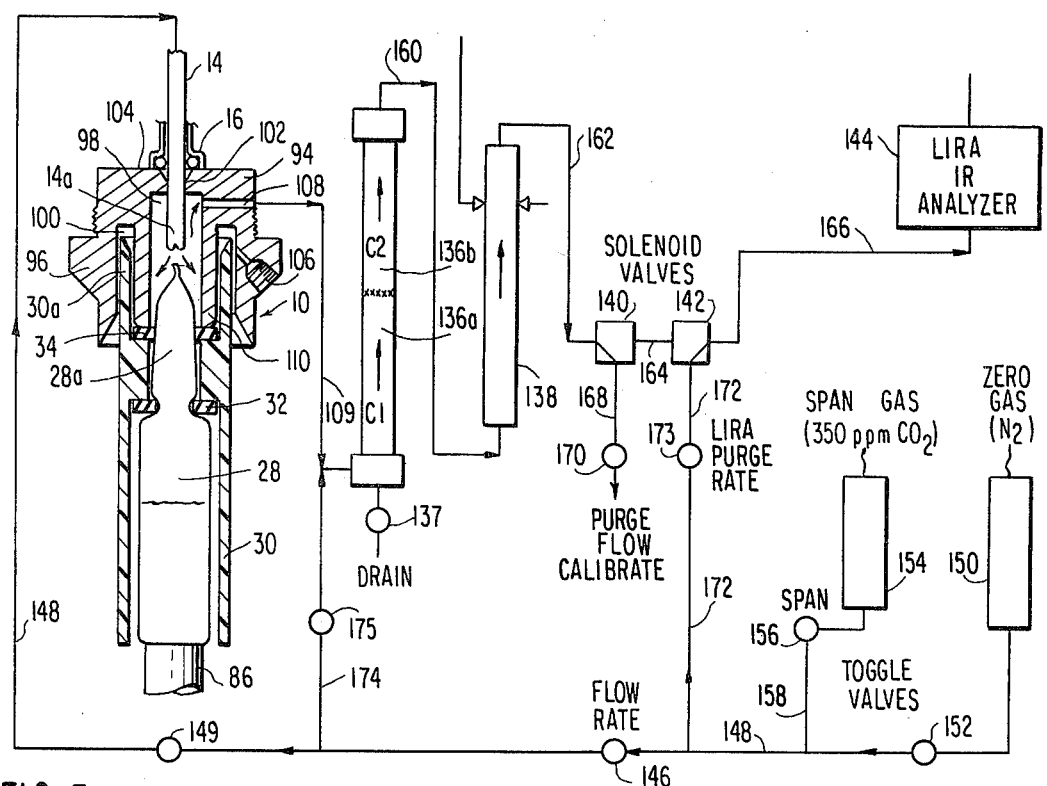
FIG. 3
FIG. 4
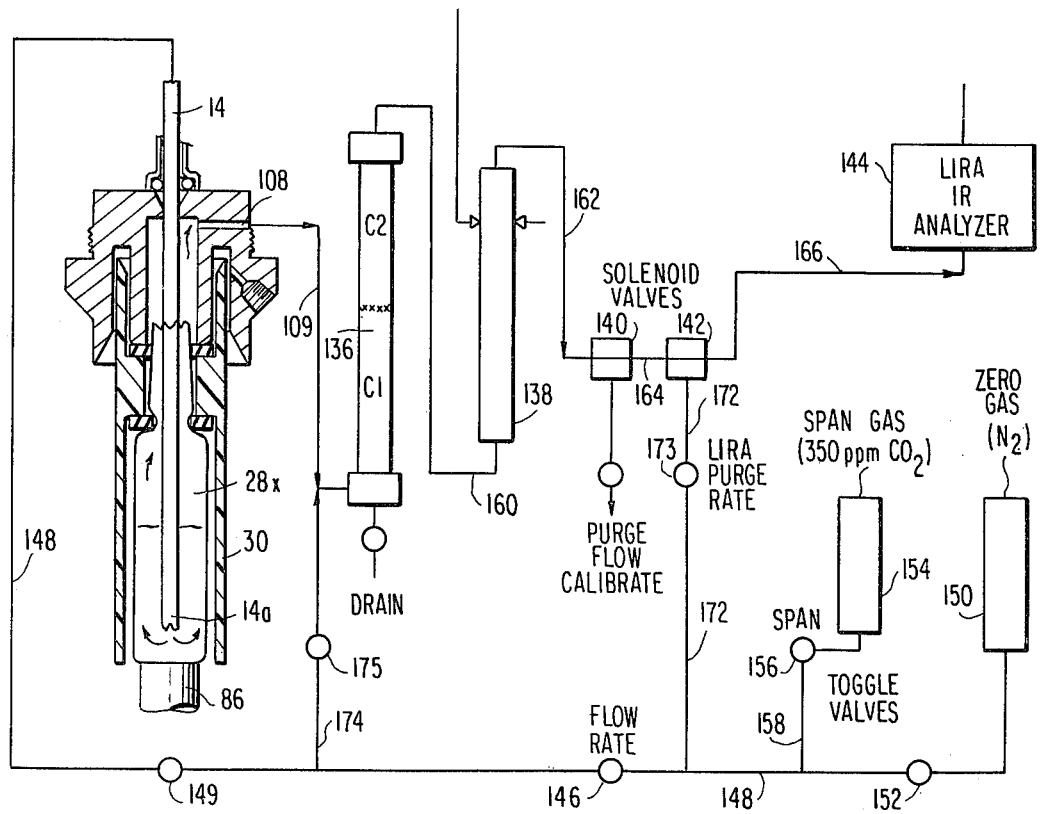

AUTOMATIC CHEMICAL ANALYSIS DEVICES AND METHODS

BACKGROUND OF THE INVENTION

1. Field of the Invention

This invention relates broadly to automatic chemical analysis devices and automated methods of chemical analysis. More particularly, it concerns the automatic testing of liquid samples sealed in glass ampoules to determine the content of a gas contained in the samples, e.g., the carbon dioxide content for determination of the carbon content of the liquid sample.

2. Description of the Prior Art

The testing of water samples to determine the carbon content is necessary in a number of different studies and activities, e.g., in limnology and oceanography studies. A variety of testing methods of this type exist, but one of the widely used procedures measures total carbon in a sample after it has been converted to carbon dioxide by wet chemistry methods (see Menzel and Vacarro; *J. of Limnology and Oceanography*, Vol. 9: 138–142; 1964).

In that wet chemistry method, inorganic carbon is first removed by purging the sample with purified oxygen. The sample is then sealed in a glass ampoule with potassium persulfate and heated to 175 deg. C. The ampoule contents are then analyzed by manually breaking off the top of the ampoule, bubbling nitrogen gas through it to expell $CO_2$ which is then typically passed to a nondispersive infrared analyzer to measure the quantity of $CO_2$. An analysis performed in this manner requires much manual handling of test items so it is very time consuming and tedious. Hence, there has existed a need for improvements in such type of chemical analysis so that the procedure can be automated to free the laboratory personnel for other duties.

The general concept of automated chemical analysis is not new (see U.S. Pat. No. 3,269,800). Also, it is known to use revolving turrets or carousels to move sample vails, test tubes, etc. seratium into position at a work station for the withdrawal of test portions, to perform tests at the station or the like (see U.S. Pat. No. 4,166,094). Moreover, automated chemical analyzers have been devised that utilize advanced electronic circuits to control movement of test elements, the flow of reagents, the performance of test steps, etc. (see U.S. Pat. No. 4,168,955). Particularly in the medical field there has been many innovations relating to automated chemical analysis equipment (see U.S. Pat. No. 3,883,305).

Notwithstanding all the research and development on automated chemical analysis, this present invention provides still further improvements on automated chemical analysis methods and automatic chemical analysis devices.

OBJECTS

A principal object of the invention is to provide new improvements in automated chemical analysis devices and methods.

Further objects include the provision of:

1. New apparatus for the automatic analysis of a multiplicity of liquid samples for their content of a specified gas, particularly for $CO_2$ content in a procedure for the determination of carbon in a liquid sample.

2. New methods for the automatic analysis of a multiplicity of liquid samples for their content of a specified gas.

3. New apparatus that may be utilized to up-grade available analysis apparatus for the determination of gas content of liquid samples for a specified gas content to automate a major portion of the test procedure.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The foregoing objects are accomplished in part in accordance with the invention by the provision of automatic chemical analysis apparatus which comprises a turret journaled in a base plate for rotation about a vertical axis, the turret having a plurality of peripheral cavities to receive and transport liquid sample ampoules encased in tubular sleeves that include at least one interior resilient ring to from a fluid-tight seal between each sleeve and ampoule encased therein, conveyor means to deliver said sleeve encased ampoules into the turret cavities, means to index seriatum the turret cavities into position at a work station, a smash unit into which the upper ends of the sleeve and encased ampoule positioned at the work station may be inserted to create a fluid-tight chamber, the smash unit having a gas exit line connected with the chamber through a wall thereof and a purge tube inlet in the top thereof, plunger means at the work station to raise the sleeve encased ampoule located in the turret cavity at the work station and insert same into the smash unit, an elongated purge tube positioned vertically above the smash unit with the lower end thereof extending through the tube inlet into the chamber, seal means to provide a fluid-tight seal between the purge tube and the tube inlet, means to move the purge tube longitudinally between a upper position where its lower end, while within said chamber, is above the top end of the ampoule located in the chamber and a lower position where its lower end extends into the ampoule near the bottom thereof, movement of said purge tube from the upper position to the lower position serving to break the top end of the ampoule, tube means to connect the purge tube to a gas source for introduction of gas into the chamber and the ampoule positioned therein, and a discharge station at which sleeve encased ampoules are removed from said turret cavities.

In a preferred embodiment of the invention the discharge station comprises a hole in the base plate in the path of travel of the turret cavities so that when the cavities are indexed to the discharge station the sleeve encased ampoules drop out of the cavities through the hole. Further, the discharge station may include a chute beneath the hole to guide sleeve encased ampoules away from the hole.

In a further embodiment the plunger means moves between an upper position which raises the sleeve encased ampoule into the smash unit inserted position and a lower postion in which the plunger means is out of contact with the sleeve encased ampoule and comprises a fluid operated piston to move the plunger means between the upper and lower positions. Also the plunger means further includes solenoid valves and limit switches to operate the valves to control movement of the piston between the upper and lower positions.

Preferably the purge tube comprises a fluid operated piston to move the purge tube between its upper and lower positions and it further includes solenoid valves and limit switches to operate the valves to control movement of the piston between the upper and lower positions. Also the smash unit includes a inlet for pressurized gas by which sleeve encased ampoules may be blown free of the smash unit at the completion of the testing of the liquid sample in the ampoule.

The stated objects are also in part accomplished by the use of new automated analysis methods that comprise the steps of providing a plurality of ampoules containing samples of liquid to be analyzed, encasing each ampoule in a tubular sleeve and forming a fluid-tight seal between the inside of each sleeve and the outside of each ampoule, positioning a sleeve encased ampoule at a work station, inserting at the work station a sleeve and the encased ampoule into an enclosed chamber while forming a fluid-tight seal between the chamber and the inserted sleeve and ampoule, removing any atmospheric air that may be in the sealed chamber as a result of inserting the ampoule, forcing a purge tube against the top end of the ampoule to break off its top end to open the ampoule and then lowering the end of the tube into the opened ampoule, introducing a stream of a gas via the purge tube into the liquid sample contained in the opened ampoule, withdrawing a stream of gas from the chamber and delivering it to a gas analysis unit, removing the opened ampoule and its encasing sleeve from the work station, positioning a another sleeve encased ampoule at the work station and repeating the aforesaid inserting though removing steps thereon.

BRIEF DESCRIPTION OF THE DRAWINGS

A more complete understanding of the invention may be had by reference to the accompanying drawings in which:

FIG. 3 is a partially diagramatic view and partially sectional view showing the smash unit of the device with the purge tube in its upper position.

FIG. 4 is a view similar to FIG. 3 with the purge tube at its lower position.

DESCRIPTION OF PREFERRED EMBODIMENTS

Figure 1:
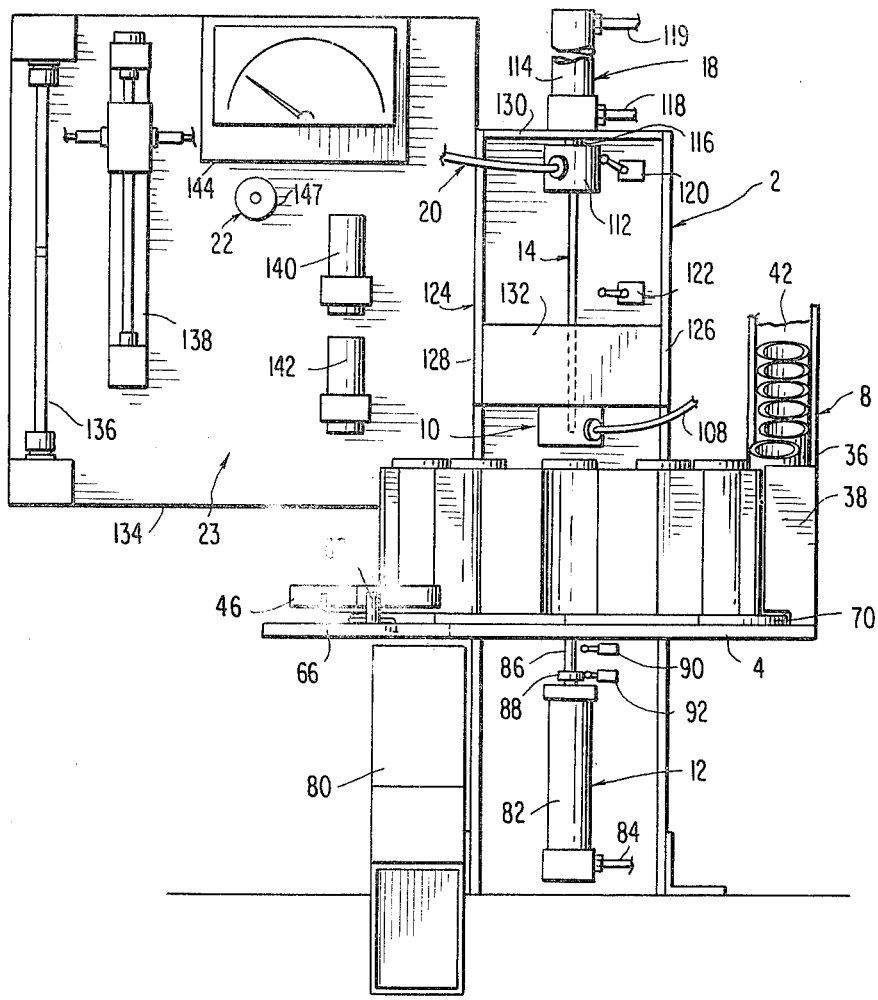
FIG. 1 is an elevational view of a chemical analysis device constructed in accordance with the invention.

With reference to the drawings, the chemical analysis device 2 basically comprises a planar base plate 4, a turret 6, conveyor means 8, a smash unit 10, plunger means 12, purge tube 14, seal means 16, purge tube movement means 18, tube 20 connected to gas source unit 22 and gas analyzer unit 23.

The turret 6 has a central shaft 24 that is journaled in the base plate 4 for rotation and a plurality of peripheral cavities 26 to receive and transport liquid sample ampoules 28 encased in tubular sleeves 30. The ampoules are preferably made of glass and the sleeves of plastic, e.g., polyvinyl chloride plastic. Resilient sealing rings 32 and 34 are provided on the interior of the sleeves 30 to form a fluid-tight seal between each sleeve 30 and ampoule 28 encased therein.

Figure 5:
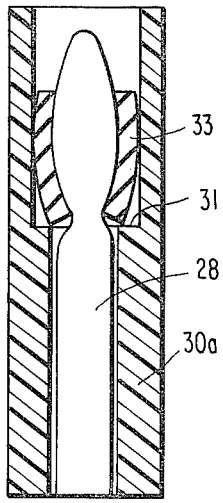
FIG. 5 is an enlarged, fragmentary, sectional view of a modified form of ampoule and sleeve seal.

FIG. 5 shows a modified form of sleeve/ampoule sealing arrangement. Here, the sleeve 30a is provided with a ledge 31 between an upper, larger bore and a lower smaller bore in the sleeve 30a. A single section of rubber tubing 33 surrounds the ampoule 28 and this forms a top and bottom seal similar to the seals formed by rings 32 and 34. The ampoule 28 with the sealing member 33 in place about it is loaded from the top into the sleeve 30a, drops down upon ledge 31 making this modification easy to load. Also the sealing member 33 is easily cleaned and the sleeve 30a is easy to make and to clean.

The conveyor means 8 comprises an inclined track 36 with an arcuate member 38 at the exit end 40. The sleeve encased ampoules 28 are loaded into the inlet end 42 of the channel 36, slide down to the member 38 and pass one at a time into an empty cavity 26 in the turret 6.

The turret 26 transports the encased ampoules 28 to a work station located beneath the smash unit 10 by rotation about the shaft 24. Such rotation is step-wise and is produced by the indexing means 44 which comprises latch 46, second latch 47, piston 48, piston rod 50, toggle 52 and limit switches 54 and 56. Line 57 supplies compressed air to move the piston 48 out; it is returned by spring action. The compressed air pressure to piston 48 and others used in the system is the same and the pistons are sized so that the force to be delivered will be adequate for the required job.

The toggle 52 pivots on the pin 58 fixed to the end of the rod 50 and is biased in a counterclockwise direction by the spring 60. A small roller 62 is carried on the free end of the toggle 52.

The latch 46 is pivoted on the pin 64 fixed to the plate 4 and is biased in a clockwise direction by the spring 66 against the stop pin 68. The second latch 47 made of plastic and self-springing is also pivoted on pin 64 beneath latch 46. This falls into place behind teeth 72 when the proper position of the turret 26 is attained. This latch 47 prevents the turret 26 from moving clockwise when piston 48 retracts at the end of the cycle and is not functional in attaining precise positioning of the turret 26. Should the turret move any appreciable amount in the clockwise direction, the next tooth 72 could not be engaged by roller 62. The cycle would restart, piston 48 would extend, but roller 62 would re-engage the same tooth it had just left resulting is an analysis of the same vial and erroneous data would result.

Figure 2:
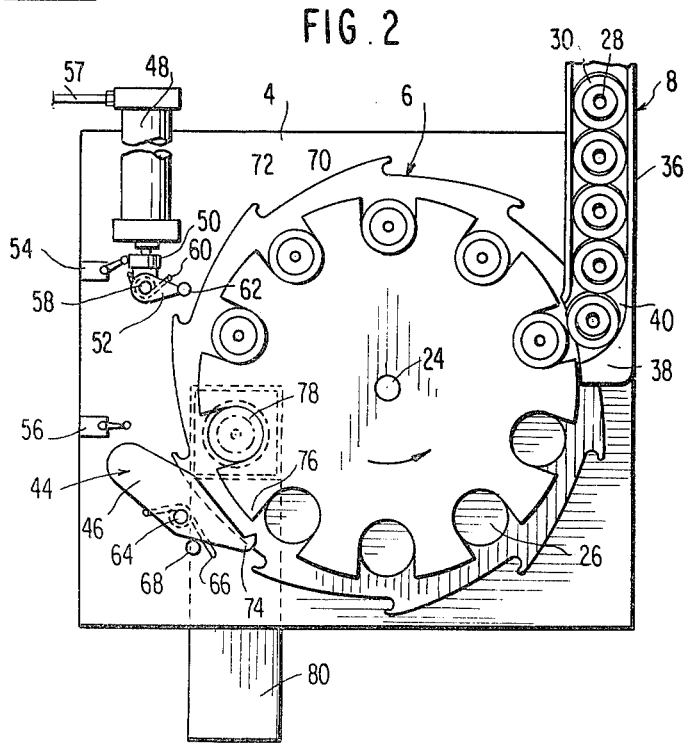
FIG. 2 is a plan view of the device of FIG. 1.

The base 70 of the turret 6 has peripheral teeth 72 equal in number to the number of cavities 26. FIG. 2 shows piston rod 50 in the retracted position engaging limit switch 54. When the piston 48 moves the rod 50 toward the extended position (not shown) the roller 62 will engage one of the teeth 72 and rotate the turret 6 in the direction of the arrow. As the rod 50 approaches full extension, the toggle 52 will contact latch 46 and rotate it counterclockwise and cause the hook-end 74 to move into the path of and then engage the trailing edge 76 of one of the cavities 26 to thereby stop further rotation of the turret 6. At the same time the rod 50 will engage the limit switch 56 to signal the control circuitry that the ampoule is properly positioned at the work station and the process may proceed. The piston rod 50 does not retract, but remains pressurized, locking the turret in that position. A counterclockwise force is applied to the turret 26 (looking from above) through roller 62, balanced by a clockwise force through latch 46. This arrangement insures proper position will be maintained through the balance of the operation on the ampoule at the work station.

The latch 46 is located on the plate 4 so that its stoppage of the turret will position one of the ampoule filled cavities at the work station beneath the smash unit 10. When the rod 50 retracts, spring 66 will return latch 46 to the position shown in FIG. 2.

There is a hole 78 in the plate 4 in the path of travel of the cavities 26 and as the cavities are indexed to this discharge station the sleeve encased ampoules 28 drop through the hole 78 into the chute 80 to be collected in a container (not shown) for recovery of the sleeves 30 and discard of the opened ampoules 28.

The plunger means 12 comprises a cylinder 82 provided with fluid line 84, a piston rod 86, a contact ring 88, upper limit switch 90 and lower limit switch 92. Compressed air applied through line 84 raises the rod 86. A spring within the cylinder 82 (not shown) returns the rod to its lower position.

The smash unit 10 comprises a cylindrical housing 94 having an integral collar 96, a central cylindrical chamber 98, a circular slot 100 concentric with the chamber 98, a circular hole 102 in its top 104, pressurized gas inlet 106 connected to line 107 and gas exit 108 connected to line 109.

The rod 86 moves up and down between an upper position where ring 88 contacts switch 90 and a lower position where the ring 88 contacts switch 92. In the upper position as seen in FIG. 3, the rod 86 inserts the ampoule 28 and the sleeve 30 into smash means 10. The top end 30a of the sleeve 30 enters the circular slot 100 so the bottom end of the wall 110 between slot 100 and chamber 98 makes sealing contact with the resilient ring 34 and that ring together with ring 32 serve to form a fluid-tight chamber around and above the top end 28a of the ampoule 28.

The elongated purge tube 14 is positioned vertically above the smash unit 10 with its lower end 14a extending through the seal means 16 into the chamber 98. The tube 14 moves between an upper position (see FIG. 3) where the lower end 14a is above the top end 28a of the ampoule 28 housed in the chamber 98 and a lower position (see FIG. 4) where its lower end extends into the opened ampoule 28x near the bottom thereof. The upper end of the tube 14 is fitted with sealed collar 112 to which tube 20 is connected to enable gas from gas source unit 22 to be fed though the hollow tube 14 and into the chamber 98 or ampoule 28.

The purge tube movement means 18 comprises the cylinder 114, a piston rod 116, fluid lines 118 and 119, upper limit switch 120 and lower limit switch 122. The collar contacts switch 120 when tube 14 is raised by means 18 to its upper position and switch 122 when tube 14 is at its lower position.

All of the portions of device 2 located above the work station are supported on frame 124 which comprises side plates 126 and 128, top plate 130 and transverse plate 132.

The gas analyzer unit 23 comprises a panel 134, a gas drying column 136, a rotameter 138, solenoid valves 140 and 142 and an infra-red ray LIRA analyzer 144. Analyzer 144 is a commercially available piece of apparatus and is related to the present invention only as a means to analyze the stream of gas automatically provided by the new methods and devices of the invention.

The gas drying column 136 has an unpacked lower section 136a, an upper section 136b packed with particulate drying material and a drain valve 137 at its base.

The gas source unit 22 comprises a needle valve 146 which is positioned behind panel 134 with its rotary handle 147 extending though the panel so the needle valve may be operated from the front of the panel 134. The needle valve 146 is connected through a gas line 148 to a tank 150 of dry, compressed nitrogen gas equipped with a toggle valve 152. Line 148 also includes a toggle valve 149 downstream of needle valve 146. Toggle valves of the device serve to full open or full close lines to begin or end operations or for other purposes.

The gas source unit 22 also includes a tank of "span" gas 154 connected by toggle valve 156 and line 158 to the gas line 148. The so-called span gas is a precise mixture of $CO_2$ and $N_2$ used to calibrate the LIRA IR analyzer. Additionally, there is a source of compressed air (not shown) connected to line 159 to provide the pressure to work the various pistons of the system.

The drying column 136 is connected via line 160 to the rotameter 138 which, in turn, connects via line 162 to valve 140, line 164 to valve 142 and line 166 to analyzer 144.

For calibration purposes to be described later, there are some specific plumbing arrangements, Thus, fluid line 162 can be connected by valve 140 to ambient via line 168 and needle valve 170. Also, fluid line 166 can be connected through valve 142 and line 172 into line 148. The line 172 includes a needle valve 173 to adjust the rate of fluid flow in line 172. Further, line 174 and toggle valve 175 connect rotameter 136 directly with the line 148 by-passing the unit 10.

The purpose of the rotameter 138 is to verify the flow rate of gas in the system. This is done by sensing the presence or absence of the rotameter ball at a predetermined position in a light beam. In place of the rotameter, a pressure differential type flow sensing unit (not shown) may be used alone or in combination with the rotameter. In any case, the purpose will remain the same, i.e., to assure the proper gas flow rate before the ampoule is broken and $CO_2$ analysis commences.

As already stated various other modifications of the new systems are possible and will occur to those skilled in the art from this disclosure. DC current is preferred for use in the systems, e.g., to actuate the solenoids because this tends to produce less disturbance to the LIRA test circuitry than does AC current which can cause small errors in test results. However, the new devices have been successfully operated with all AC current.

Another example of modification involves the method of determining the point at which the $CO_2$ analysis is considered complete. As disclosed in the drawings, this is done by sensing the position of a needle on a meter as it approaches zero. This monitors a mechanical result (needle movement). Instead, determing the analysis end-point can be done by monitoring the electrical output of the LIRA analyzer directly.

The analysis device 2 uses simple consecutive electrical logic (a step cannot be performed until the previous step is completed) and low pressure air for motion. The device contains all valving necessary for operation of the air powered cylinders and for nitrogen gas flow switching. Gas connections are provided for incoming nitrogen, incoming span gas and output to the LIRA CO₂ analyzer.

Figure 6:
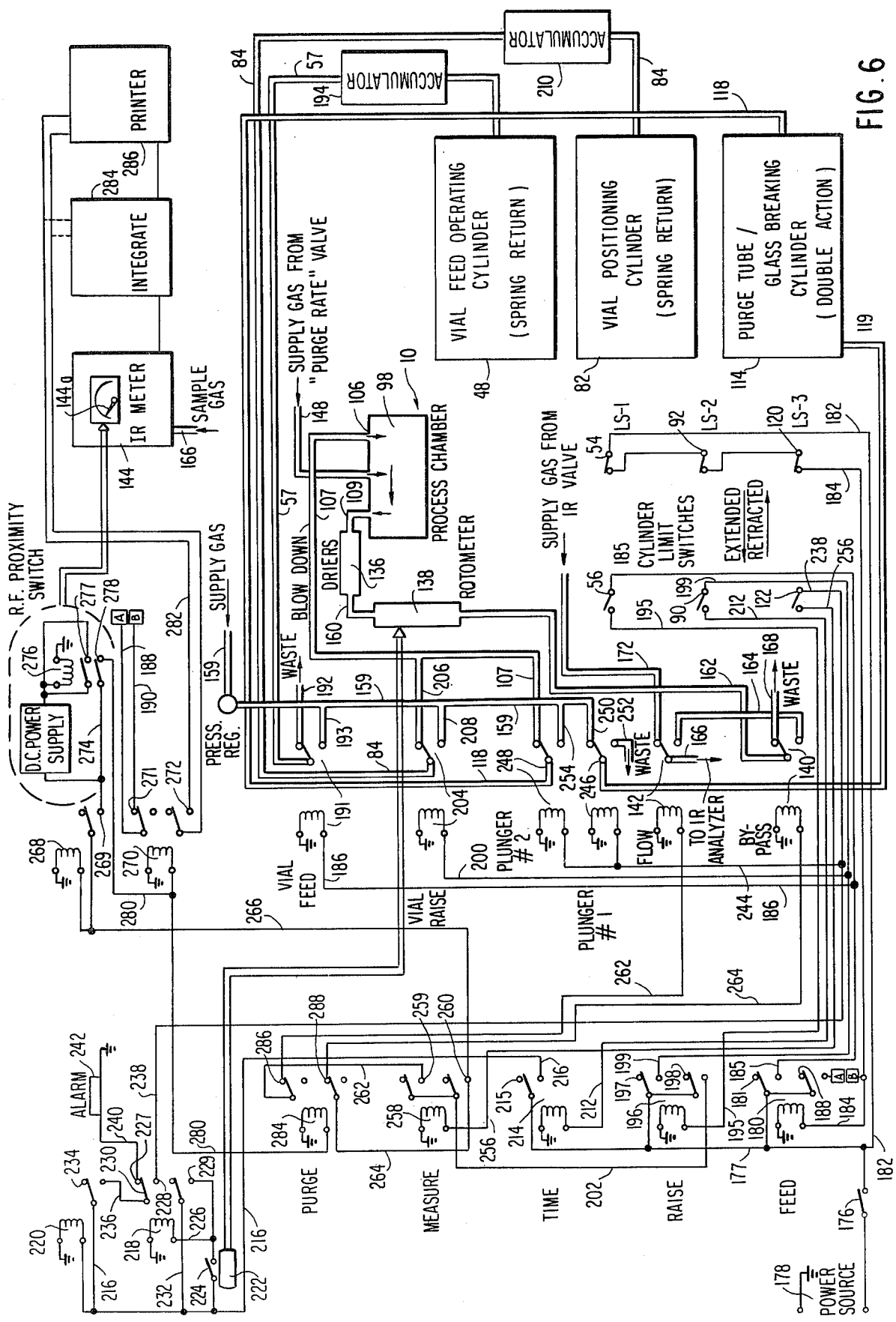
FIG. 6 is a schematic diagram of electrical and plumbing elements of the device of FIG. 1.

Operation of the device is explained below with particular reference to FIG. 6. In FIG. 6 some of the lines are not connected for the sake of clarity, e.g., line 166 is broken at the bottom and resumed again at the top of the figure. Also, the symbols "A" and "B" at the bottom left of the figure are to designate continuation of their respective wires to the symbols "A" and "B" at the top center of the figure.

Ampoules 28 are snapped into sleeves 30 so that resilient rings 32 and 34 seal the ampoules to the sleeves. Alternatively, ampoules 28 will be loaded into sleeves 30a as previously described. The encased ampoules are then loaded onto the sloping track 36. A heavy steel roller (not shown) is loaded last to assure the gravity feed of the encased ampoules.

In preparation for making analysis with the device 2 it is necessary to purge various sections of the fluid lines, to calibrate the LIBRA analyzer and to adjust the flow rate of purge gas. At this point, solenoid valves 140 and 142 will not be energized so fluid line connections through them will be as shown in FIGS. 3 and 6. With valves 152 and 146 closed, span gas can be passed to analyzer 144 via lines 148, 172 and 166 to calibrate the analyzer for the current measurements. When this calibration is completed, valve 156 is closed and valve 152 is opened to allow zero gas (compressed, dry nitrogen gas) from source 150 to flow via needle valve 146 at a controlled rate through line 148. With toggle valve 149 closed and toggle valve 175 open, zero gas is passed via line 174, column 136 and line 160 to the rotameter 138, then line 162, valve 140, line 168 and needle valve 70 to ambient. The purpose of this is to adjust the rate of flow of zero gas in the system prior to beginning an analysis run. In making this adjustment, valve 170 is set at a throttle setting so that its resistance to the gas flow will be comparable to the resistance offered during analysis by the analyzer 144 and other elements downstream of valve 140. When the gas flow rate has reached the proper value as noted by the rotameter, toggle valve 175 is closed, valve 149 is opened and the system is ready for testing operation.

The device 2 is turned on by closing switch 176 which connects bus line 177 to the power source 178. At that time the limit switches 54, 92 and 120 will be closed and limit switches 56, 90 and 122 will be open.

When switch 176 closes, solenoid DPST switch 180 will be energized through wires 182 and 184 and its contacts 181 and 183 will move into closed position. This will cause wires 185, 186, 188 and 190 to be energized.

The current from wire 186 will energize solenoid valve 191 to switch line 57 from ambient (waste) line 192 into connection via nipple 193 with power gas line 159. This causes compressed air to flow through line 57 via accumulator 194 to cylinder 48 thereby moving rod 50 to its extended position and indexing a new ampoule 28 into position at the work station beneath smash unit 10 and close switch 56. Although switch 54 opens as rod 50 moves out, wire 184 remains energized from bus 176 via contact 183 and the loop formed by wires 188 and 190 so the piston rod 50 does not retract locking the turret 26 in its proper work station position.

The closing of switch 56 sends current through wire 195 to solenoid DPST switch 196 closing contacts 197 and 198. Contact 197 energizes wires 199 and 200; contact 198 energizes wire 202.

The current in line 200 operates solenoid valve 204 to switch fluid line 84 from connection to line 107 through nipple 206 over to work gas supply line 159 via nipple 208. Line 84 then pressurizes cylinder 82 via accumulator 210 thereby causing the piston rod 86 to move upward. This opens switch 92 and switch 90 closes when the rod 86 reaches its top position. This elevates the ampoule 28 and casing 30 and inserts them into the smash unit 10 as shown in FIG. 3 forming the closed chamber 98.

Closing switch 90 energizes wire 212 to actuate solenoid SPST switch 214 and close contact 215 to connect wire 216, which leads to time delay relays 218 and 220, onto the bus 177.

As previously explained, the flow rate of zero gas (N₂) flowing in the system is measured by rotameter 138. The rate level of the rotameter is detected by photocell proximity unit 222 that includes the switch 224. If the flow rate if within the permitted limits, switch 224 will close to actuate time delay relay 218 which is a DPDT switch with contacts 227, 228 and 229. If switch 224 remains closed for the time dealy of relay 218, e.g., ten seconds, the relay will operate and switch blade 230 will move from contact 227 to contact 228. Also, contact 229 will be connected to wire 232. This latter connection will continue to energize relay 218 via wires 232 and 226 throughout the remainder of the test cycle even if switch 224 should open.

Relay 220 is a SPST switch with contact 234 and has a time delay longer than relay 218, e.g., 15 secs. When it closes wire 236 will be energized via wire 216 and contact 234. If relay 218 has thrown, wire 238 will be energized via wire 236 and contact 228. If relay 218 has not thrown because switch 224 did not close for the required time, wire 240 will be energized to operate the alarm 242 to summon an attendant to determine if there has been some malfunction.

The time delay of relay 220 provides the time in which the chamber 98 and downstream lines, e.g., line 109, are purged with zero gas. It should be understood that once the zero gas flow has been established as previously described, this gas flow continues throughout the entire analysis operations.

Energizing wire 238 also energizes wire 244. This in turn actuates solenoid valves 246 and 248. Actuation of valve 246 switches line 119 from power gas line 159 via nipple 250 over to ambient (waste) line 252. Actuation of valve 248 switches line 118 from line 107 over to power gas line 159 via nipple 254 which pressurizes cylinder 114 to move the purge tube 14 downward to smash the top 28a of the ampoule 28 and position the lower end 14a of tube 14 close to the bottom of the ampoule 28 as seem in FIG. 4. This movement of tube 14 will open switch 120, close switch 122, and energize wire 256. The current in wire 256 will actuate solenoid DPST switch 258 with contacts 259 and 260. Closing contact 259 energizes wire 262 to actuate solenoid valve 142. Closing contact 260 energizes wire 264 to actuate solenoid valve 140. Actuation of these valves switches the device from the mode shown in FIG. 3 to the mode shown in FIG. 4. Thus, line 162 moves from line 168 to connect to line 164 and line 166 moves from line 172 to connect to line 164 so that the flow of gas from chamber 98 now flows through the analyzer 144.

Energizing line 266 actuates time delay relay 268, which is a SPST switch with contact 269. Contact 269 connects to wire 274 that leads to proximity switch 276 having contacts 277 and 278. The circuit for switch 276 senses the position of the needle 144a of the meter 144. As a new flow of gas from line 166 flows into the meter 144, the needle will move from zero value up scale. The time delays of relays 268 and 270 permit the needle to move out of the sensing area of proximity switch 276 on the up-swing, but allow the switch 276 to operate on the needle down-swing so that the end-point of a test can be detected to shut off that test and rearm the device 2 for the analysis of a new ampoule.

As the $CO_2$ content of the gas flowing into the analyzer 144 through line 166 drops, the needle 144a swing back toward zero. At some predetermined reading slightly above zero the proximity switch 276 will detect the presence of the needle and the switch will close contacts 277 and 278. Contact 278 will energize wire 280 to actuate relay 270, which is a DPDT switch with contacts 271 and 272. After its time delay (10 secs.) relay 270 contact 272 will close closing the circuit of wire 282 causing the integrator 284 and printer 286 to operate to record the results of the just completed test. At the same time, contact 271 will open to open the circuit in wires 188 and 190 thereby deenergizing the switch 180. However, during the delay in operation of relay 270, current flowing in wire 280 will actuate solenoid DPST switch to open wire 262 at contact 286 and wire 264 at contact 288 to deenergize solenoid valves 140 and 142 returning them to the purge mode as shown in FIG. 3.

The device 2 has now been restored to the start-up mode so that the turret 6 will move one notch forward placing a new ampoule at the work station and the test procedure begins anew.

The embodiments of the invention in which an exclusive property or privilege is claimed are defined as follows:

1. An automatic chemical analysis device comprising:
   a turret journaled for rotation about a vertical axis, said turret having a plurality of peripheral cavities to receive and transport liquid sample ampoules encased in tubular sleeves,
   resilient sealing means to form a fluid-tight seal between each sleeve and ampoule encased therein,
   conveyor means to deliver said sleeve encased ampoules into said turret cavities,
   means to index seriatum said turret cavities into position at a work station,
   a smash unit into which the upper ends of the sleeve and encased ampoule positioned at said work station may be inserted to create a fluid-tight chamber, said smash unit having a gas exit line connected with said chamber through a wall thereof and a purge tube inlet in the top thereof,
   plunger means at said work station to raise the sleeve encased ampoule located in said turret cavity at said work station and insert same into said smash unit,
   an elongated purge tube positioned vertically above said smash unit with the lower end thereof extending through said tube inlet into said chamber,
   seal means to provide a fluid-tight seal between said purge tube and said tube inlet,
   means to move said purge tube longitudinally between a upper position where its lower end, while within said chamber, is above the top end of the ampoule located in the chamber and a lower position where its lower end extends into said ampoule near the bottom thereof, movement of said purge tube from said upper position to said lower position serving to break said top end of said ampoule,
   tube means to connect said purge tube to a gas source for introduction of gas into said chamber and said ampoule positioned therein, and
   a discharge station at which sleeve encased ampoules are removed from said turret cavities.

2. The device of claim 1 wherein said turret is journaled in a base plate and said discharge station comprises a hole in said base plate in the path of travel of said turret cavities so that when said cavities are indexed to said discharge station said sleeve encased ampoules drop out of said cavities through said hole.

3. The device of claim 2 wherein said discharge station includes a chute beneath said hole to guide sleeve encased ampoules away from said hole.

4. The device of claim 1 wherein said plunger means moves between an upper position which raises said sleeve encased ampoule into said smash unit inserted position and a lower postion in which said plunger means is out of contact with said sleeve encased ampoule and comprises a piston to move said plunger means between said upper and lower positions.

5. The device of claim 4 wherein said plunger means further includes solenoid valves and limit switches to operate said valves to control movement of said piston between said upper and lower positions.

6. The device of claim 1 wherein said means to move said purge tube comprises a piston to move said purge tube between said upper and lower positions.

7. The device of claim 6 wherein said means to move further includes solenoid valves and limit switches to operate said valves to control movement of said piston between said upper and lower positions.

8. The device of claim 1 wherein said smash unit includes an inlet for pressurized gas by which sleeve encased ampoules may be blown free of said smash unit at the completion of the testing of the liquid sample in said ampoule.

* * * * *